(12) United States Patent
Wang et al.

(10) Patent No.: US 8,486,482 B2
(45) Date of Patent: Jul. 16, 2013

(54) METHODS TO IMPROVE ADHESION OF POLYMER COATINGS OVER STENTS

(75) Inventors: Yunbing Wang, Sunnyvale, CA (US); Daniel A. Castro, Santa Clara, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 128 days.

(21) Appl. No.: 13/175,689

(22) Filed: Jul. 1, 2011

(65) Prior Publication Data

US 2012/0003379 A1 Jan. 5, 2012

Related U.S. Application Data

(62) Division of application No. 11/953,657, filed on Dec. 10, 2007, now Pat. No. 7,998,524.

(51) Int. Cl.
*A61L 33/00* (2006.01)
(52) U.S. Cl.
USPC .......... 427/2.1; 424/423; 424/94.4; 427/2.24; 514/171; 514/291

(58) Field of Classification Search
USPC . 427/2.1, 2.24, 2.25; 424/423, 94.4; 514/171, 514/291
See application file for complete search history.

(56) References Cited

U.S. PATENT DOCUMENTS

| | | | |
|---|---|---|---|
| 5,468,560 A | 11/1995 | McPherson et al. | |
| 7,329,366 B1 | 2/2008 | Gale et al. | |
| 7,998,524 B2 | 8/2011 | Wang et al. | |
| 2001/0000076 A1 | 3/2001 | Jansen et al. | |
| 2006/0034931 A1 | 2/2006 | Hansen | |
| 2007/0202147 A1* | 8/2007 | Kleiner et al. | 424/423 |
| 2007/0281073 A1 | 12/2007 | Gale et al. | |
| 2007/0286941 A1 | 12/2007 | Huang et al. | |
| 2008/0001333 A1 | 1/2008 | Kleine et al. | |

* cited by examiner

*Primary Examiner* — David Turocy
*Assistant Examiner* — Andrew Bowman
(74) *Attorney, Agent, or Firm* — Squire Sanders (US) LLP

(57) ABSTRACT

Methods are disclosed to improved adhesion of polymer coatings over polymer surfaces of stents which include plasma treatment, applying an adhesion promoting layer, surface treatments with solvents, and mechanical roughening techniques.

5 Claims, 9 Drawing Sheets

METHODS TO IMPROVE ADHESION OF POLYMER COATINGS OVER STENTS

This is a divisional application of application Ser. No. 11/953,657 filed on Dec. 10, 2007, now U.S. Pat. No. 7,998,524 which is incorporated by reference herein.

BACKGROUND OF THE INVENTION

1. Field of the Invention

This invention relates to adhesion of coatings for implantable medical devices composed of bioabsorbable polymers.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug. Potential problems with therapeutic coatings for polymeric implantable medical devices, such as stents, include insufficient toughness, slow degradation rate, and poor adhesion.

SUMMARY OF THE INVENTION

Various embodiments of the present invention include a method of improving the adhesion of a polymer coating layer to a stent surface comprising: providing a stent formed from a substrate polymer; treating a polymer surface of the stent with a fluid capable of swelling the substrate polymer, dissolving the substrate polymer, or both, wherein the treating increases the roughness of the polymer surface; and forming a coating comprising coating polymer on the treated stent surface, the increased surface roughness enhancing the adhesion of the coating polymer to the stent surface.

DETAILED DESCRIPTION OF THE INVENTION

Various embodiments of the present invention include an implantable medical device with a polymer surface that has been modified to improve adhesion between the surface and an applied coating. In some embodiments, the surface of the device is modified using a plasma treatment, mechanical roughening, or treating the surface with solvents to etch the surface. Other embodiments are directed to an adhesion promoting layer between the surface and a therapeutic layer. The various embodiments will be discussed below, along with examples.

The polymeric surface may be a surface of a polymer coating disposed above a substrate that can be composed of metal, polymer, ceramic, or other suitable material. Alternatively, the polymeric surface may be a surface of a polymeric substrate. "Above" a surface is defined as higher than or over a surface measured along an axis normal to the surface, but not necessarily in contact with the surface.

Figure 1:
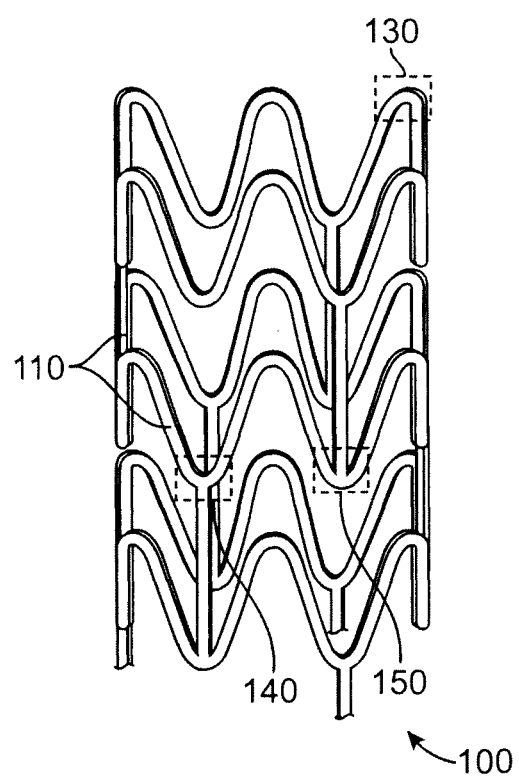
FIG. 1 depicts a view of a stent.

The present invention may be applied to implantable medical devices including, but not limited to, self-expandable stents, balloon-expandable stents, stent-grafts, and grafts (e.g., aortic grafts), and generally expandable tubular devices for various bodily lumen or orifices. A stent can have a scaffolding or a substrate that includes a pattern of a plurality of interconnecting structural elements or struts. FIG. 1 depicts a view of an exemplary stent 100. Stent 100 includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The variations in stent patterns are virtually unlimited.

In some embodiments, a stent may be fabricated by laser cutting a pattern on a tube or a sheet rolled into a tube. Representative examples of lasers that may be used include, but are not limited to, excimer, carbon dioxide, and YAG. In other embodiments, chemical etching may be used to form a pattern on a tube.

An implantable medical device can be made partially or completely from a biodegradable, bioabsorbable, bioerodable, biostable polymer, or a combination thereof. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis, enzymolysis, oxidation, and metabolic processes.

As indicated above, a medicated implantable medical device, such as a stent, may be fabricated by coating the surface of a stent with a drug. For example, a device can have a coating including a drug dispersed in a polymeric carrier disposed over a substrate of the stent. Such a coating layer may be formed by applying a coating material to a substrate of an implantable medical device, such as a stent. The coating material can be a polymer solution and a drug dispersed in the solution. The coating material may be applied to the stent by immersing the stent in the coating material, by spraying the material onto the stent, or by other methods known in the art. The solvent in the solution is then removed, for example, by evaporation, leaving on the stent surfaces a polymer coating impregnated with the drug.

Stents are typically subjected to stress during use. "Use" includes manufacturing, assembling (e.g., crimping a stent on balloon), delivery of a stent through a bodily lumen to a treatment site, deployment of a stent at a treatment site, and treatment after deployment. Both the underlying scaffolding or substrate and the coating experience stress that result in strain in the substrate and coating. In particular, localized portions of the stent's structure undergo substantial deformation. For example, the apex regions of bending elements 130, 140, and 150 in FIG. 1 experience relatively high stress and strain during crimping, expansion, and after expansion of the stent.

As indicated above, a device may be composed in whole or in part of materials that degrade, erode, or disintegrate through exposure to physiological conditions within the body until the treatment regimen is completed. The device may be configured to disintegrate and disappear from the region of implantation once treatment is completed. The device may disintegrate by one or more mechanisms including, but not limited to, dissolution and chemical breakdown. The duration of a treatment period depends on the bodily disorder that is being treated. For illustrative purposes only, in treatment of coronary heart disease involving use of stents in diseased vessels, the duration can be in a range from about a month to a few years. However, the duration is typically in a range from about six to twelve months. Thus, it is desirable for polymer-based coatings and substrates of an implantable medical device, such as a stent, to have a degradation time at or near the duration of treatment. Degradation time refers to the time for an implantable medical device to substantially or completely erode away from an implant site.

Furthermore, polymer substrates and polymer-based coatings may be particularly vulnerable to mechanical instability during use of a stent. Such mechanical instability for coatings can include fracture and detachment from a substrate, for exampling, peeling. Some polymers may be susceptible to such mechanical instability due to insufficient toughness at high deformations. Additionally, detachment of coatings may be due to poor adhesion of the polymer-based coating to the substrate or another polymer layer. Therefore, polymer-based coatings are highly susceptible to tearing or fracture, and/or detachment, especially at regions subjected to relatively high stress and strain. Thus, it is important for a polymer-based coating to have good adhesion with an underlying layer or substrate and to have a high resistance to detachment in the range of deformations that occur during crimping, during deployment of a stent, and after deployment.

Accordingly, the following embodiments are directed to different methods of increasing the adhesion of coatings to the substrate by altering the surface of the substrate or by providing an adhesion promoting layer.

Surface Plasma Treatment

Certain embodiments of the invention are directed to treating a polymer surface of an implantable medical device prior to applying a coating layer to the device. The plasma treatment of the surface improves the adhesion of the coating layer applied to the plasma treated surface.

A plasma is a partially ionized gas containing ions, electrons, atoms and neutral species. Plasmas are formed when energy exceeding the ionization energy of gaseous atoms/molecules is applied to them, thereby causing ionization. Ionization results in the formation of free electrons, ionic species, photons, and free radicals. Plasmas may be characterized by the following variables: density of the neutral particles, densities of electrons and ions, energy distributions, and the degree of ionization.

To enable a gas to be ionized in a controlled and qualitative manner, the plasma formation is carried out under vacuum conditions. In exemplary plasma formation processes, a vacuum vessel is first pumped down via rotary and roots blowers, sometimes in conjunction with high-vacuum pump, to a low to medium vacuum pressure in the range of 10-2 to 10-3 mbar. The gas is then introduced into the vessel by means of mass flow controllers and valves. Exemplary gases or mixtures of gases for plasma treatment of polymers include, but are not limited to, oxygen, helium, argon, nitrous oxide, tetrafluoromethane, and air. A high-frequency generator, for example, in the kHz, MHz, or microwave range, can be then used to ionize the gas into a plasma.

In a low temperature plasma treating processes, a gas is ionized in a vacuum (typically 10 to 1000 millitorr) which creates low temperature and non-thermal equilibrium plasma. The temperature of the gas is about 30 to 50° C. above ambient.

In exemplary embodiments, the energy for ionizing or activating energy in plasma treating can come from long or short radio waves or microwaves. Typically, 40-400 kHz is used at the lower end, 13.56 MHz in the middle, and 2.54 GHz in the upper end. Most plasma treatments use 13.56 MHz. The shorter the wavelength, the greater the ionization and the more chemically active the gas becomes. In other exemplary embodiments, a plasma can be formed by applying electrical energy, including direct current (DC) and alternating current (AC).

Plasma systems generally comprise five main components: the vacuum vessel, a pumping apparatus, a gas-introduction and gas-control system, an RF generator, and a microprocessor-based system controller. Various optional parts can then be added to adapt a base system to handle particular applications or substrates, such as special barrels for small pieces, modified electrode racks, or guiding systems for textiles or fibers. A wide range of equipment is available, from smaller laboratory-scaled systems and custom-designed units to large textile treaters.

A plasma includes highly reactive particles since due to the high energy state of such particles. Thus, in some embodiments, the reactive particles react with a polymer surface without little or no damage to the bulk properties of the treated part of the surface. In exemplary embodiments, the surface modification of a treated surface may be limited to an outermost region of 10 to 1000 Å of the substrate, although the region can be greater than 1000 Å. Below the surface modified region, the polymer can be unmodified by the plasma or substantially unmodified.

In certain embodiments of the present invention, a polymer surface of an implantable medical device is treated with a plasma to modify the surface. In such embodiments, the treated surface is activated such that the treated surface is more reactive. "Activation" generally refers to increasing the chemical reactivity of a surface. The activation by a plasma treatment may be due to the replacement of surface polymer groups with chemical groups from the plasma. In these embodiments, during such activation, the plasma breaks down weak bonds in the polymer and replaces them with highly reactive amino ($-NH_2$), carbonyl ($C=O$), carboxyl ($-COOH$), and hydroxyl groups ($-OH$).

Various kinds of polymer surfaces can be activated with a plasma treatment. These include biodegradable polyesters, polyanhyrides, and polyorthoesters. In general, the specific change in substrate characteristics are determined by the type of chemical groups incorporated into the surface.

Figure 2A:
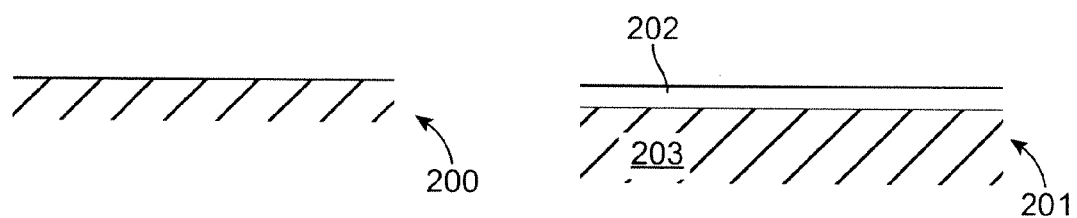
FIG. 2A depicts a polymer surface before and after plasma treatment.

FIG. 2A depicts a polymer surface 200 of a stent prior to plasma treatment and activated polymer surface 201 after plasma treatment. Plasma treated polymer surface 201 includes an activated region 202 having highly reactive functional groups. Such groups are capable of chemical bonding to a selected polymer disposed over the activated surface. A region 203 below activated region 202 can be unmodified or substantially unmodified by the plasma treatment.

Figure 2B:
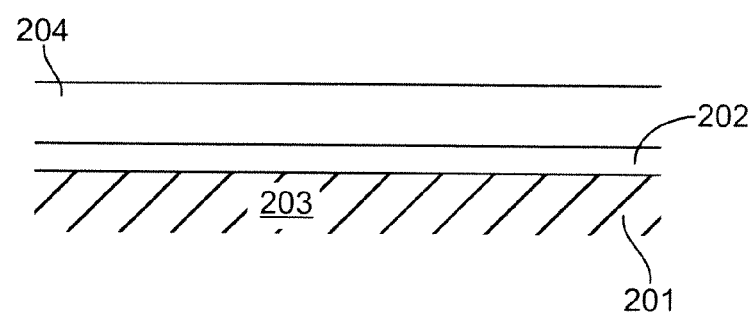
FIG. 2B is a cross-sectional view of a polymer over a plasma treated surface.

In some embodiments, the treatment of the polymer surface increases the adhesion of a polymer coating disposed over the treated surface. In such embodiments, the coating polymer is capable of chemical bonding with the highly reactive functional groups formed by the plasma. FIG. 2B depicts a polymer coating layer 204 disposed over activated region 202. The reactive functional groups of activated region 202 chemically bond to coating polymer of layer 204 in a region of layer 204 adjacent to activated region 202.

The coating polymer can include various kinds of biodegradable polymers including, but not limited to, PLLA (poly(L-lactide), PDLA (poly(D,L-lactide), PCL (polycaprolactone), PDO (polydioxanone), and PGA (polyglycolide). The copolymers of the above-mentioned polymers can include random, alternating, or block copolymers. It is believed that during formation of a polymer coating over the activated surface, the coating polymer can chemically bond to the active surface, thereby increasing the adhesion of the coating polymer to the treated surface. The increased polarity of the activated surface can also increase the adhesion through non-covalent bonding. This includes hydrogen bonding, dipolar interactions, and London van der Waals forces.

Plasma treatment is particularly advantageous for surface polymer/coating polymer combinations in which the surface and coating polymer have a low miscibility or are immiscible. For miscible coating polymer/surface polymer combinations, during the coating process, surface and coating polymer can mix in a surface region. Such mixing enhances the adhesion of the coating polymer to the surface polymer.

Exemplary Embodiment

In certain embodiments, the stent substrate or surface polymer is a semi-crystalline biodegradable polymer. In such embodiments, the semi-crystalline polymer may have Tg above human body temperature. The crystallinity may be at least 10%, 30% 50%, 60%, or greater than 60% by volume. In such embodiments, the coating polymer can have a lower crystallinity than the surface polymer or the coating polymer can be amorphous.

In an exemplary embodiment, the stent substrate polymer is PLLA and the coating polymer is PDLA. PLLA is immiscible with PDLA since PLLA is a semi-crystalline polymer and PDLA is amorphous. The PLLA stent substrate is plasma treated to activate the PLLA surface to form reactive amino (—$NH_2$), carbonyl (C=O), carboxyl (—COOH), and hydroxyl groups (—OH) on a surface of the stent substrate. The plasma treatment of the PLLA substrate surface enhances the adhesion of the PDLA surface to the substrate.

In some embodiments, the plasma treatment can modify the crystallinity of a treated surface so that a surface region has lower crystallinity. Thus, the modified surface region may be miscible with a coating polymer having a lower crystallinity than an untreated surface polymer. As a result, the adhesion of the coating polymer to the surface polymer can be enhanced due to the increased miscibility of the polymer arising from the decreased cystallinity of the surface polymer. For example, plasma treatment of a PLLA surface can form a surface region of lower crystallinity that is miscible with a PDLA coating polymer.

Figure 2C:
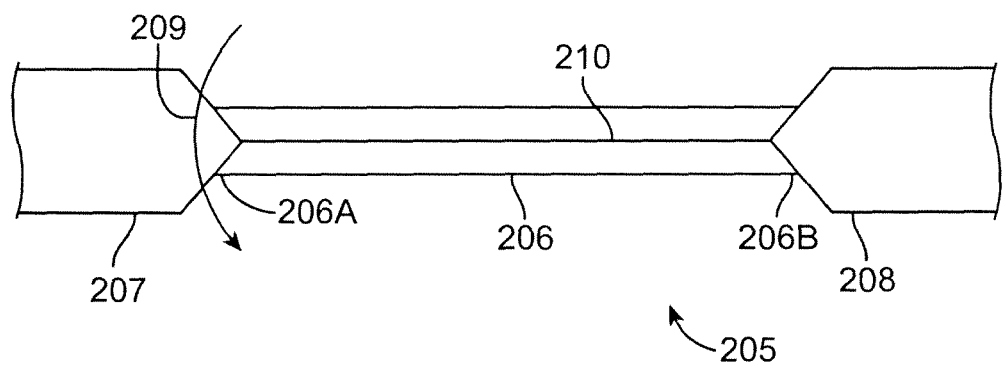
FIG. 2C depicts a stent mounted on a cone mandrel support.

In embodiments of plasma treatment, a stent can be disposed on a stent support positioned within the plasma vacuum chamber. The stent support can include various types of supports or mandrels known in the art used for spray coating stents. The mandrel can be designed so as to minimize contact area of the stent with the support to reduce or eliminate untreated areas of the stent surface. FIG. 2C depicts a schematic illustration of a stent 206 disposed on a cone mandrel support 205 including a proximal support member 207, a distal support member 208 and core wire 210 extending between the cone members. Proximal end 206A of stent 206 is supported by cone member 207 and a distal end 206B of stent 206 is supported by cone member 208. One or both of the cone support members are affixed to rotatable fixture (not shown) that allows rotation of stent 206 as shown by an arrow 209, thereby allowing a more even application of plasma treatment to stent 206.

In some embodiments, the mandrels may be made of Teflon or a metal such as stainless steel. The fixture with the mandrel/stent assemblies is placed in a Plasma Treater, such as a March Plasma C-Series Plasma Treater (St. Petersburg, Fla.). The stents are treated using a working gas in a plasma environment.

The working gas can be helium, argon, oxygen, carbon dioxide, nitrogen, nitrous oxide, ammonia, tetrafluoromethane, water vapor, air or combinations thereof In some embodiments, a working gas is supplied at a rate in the range of about 0.01 to 10 liters/minute. In further embodiments, the rate is 1 liter/minute. The gas rate is typically determined by the size of the plasma chamber and specified by the manufacturer of the plasma treater.

In certain embodiments, the pressure of the plasma chamber may be in the range of about 10 to 1000 millitorr. In some embodiments, the pressure is 100 millitorr.

The Plasma Treater may supply power in the range of about 10 to 2000 watts for about 10 to 600 seconds. Under certain embodiments, plasma conditions of about 200 watts for approximately 150 seconds are executed. Power may be supplied from a high-frequency voltage source.

One feature of plasma treatment is its short cycle time, and adequate treatment can be achieved in minutes. In some embodiments, longer plasma treatment times can result in a higher levels of surface modification with new functional groups. Excessively long exposure can cause polymer degradation and scission on the surface. Loose polymer fragments can then adversely effect the adhesion of a subsequent coating layer. The power level must be adequate to ignite' or create the plasma by ionization. Higher powers levels can create a more intense plasma with a higher concentration of reactive species. This can also lead to more energetic photons in the UV and vacuum UV range. While this can functionalize the surface, it can also, if taken to extreme, create excessive polymer degradation. In certain embodiments, the type of gas plays a critical role in the nature of the surface fuctionalization. Inert gases such as argon or helium do not actively bond to or become incorporated into the surface. They transfer energy by bombardment which creates free radicals at the surface and they also sputter the surface clean. Gases such as air, nitrogen, oxygen, nitrogen, water and $CO_2$ break down to form reactive species which functionalize the polymer surface. For example, an oxygen plasma will result in the formation of carboxyl and hydroxyl groups on the surface. Careful treatment with ammonia can lead to amino groups on the surface. Fluorine containing gases produce very reactive fluorine radicals which can etch and react with a very large range of surfaces.

Following removal of the stent from the plasma chamber, they may be coated with a polymer drug reservoir layer. In several embodiments, the coating layer is applied within 1, 2, 6, or 12 hours of the plasma treatment. The reactive groups created by plasma on the device surface may only be stable for a limited period which in some embodiments is several days. Additionally, the reactive surface of a polymer chain can change and evolve with time. Polymer chains formed within the bulk polymer can diffuse to the surface and surface modified chains can diffuse into the bulk polymer.

The polymer coating may be applied to the substrate using any of the techniques well known in the art, such as dipping or spraying the coating material onto the substrate polymer. Exemplary spray parameters are discussed in detail below. Polymer coatings applied to plasma treated surfaces should adhere more strongly, and be more likely to withstand the expansion step of implanting a medical device such as a stent.

In certain embodiments, a surface of a stent can be selectively treated with a plasma. In particular, coating on regions subjected to high strain during expansion and crimping is particularly susceptible to cracking, peeling, and delamination. In particular, surface regions of bending elements 130, 140, and 150 undergo substantial deformation during crimping and expansion. In some embodiments, selected surface regions of a polymer stent can be selectively plasma treated. In these embodiments, selective plasma treatment can be performed by reducing or preventing treatment of areas other than the selected regions. In one embodiment, a mask or covering can be disposed over the stent that allows treatment of selected regions and shields other regions from treatment. Such masks can be composed of stainless steel, aluminum, cobalt chromium alloys, titanium, niobium, tantalum, tungsten, or ceramics such as alumina, zirconia, or tungsten carbide. In some embodiments, a mask can include one or more bands that mask or shield straight portions of struts with bending portions exposed to plasma.

In further embodiments, a polymer surface of an implantable medical device can be treated with a plasma to ablate the polymer surface. In general, plasma ablation refers to removal of material from the polymer surface due to treatment of the plasma. Ablation of a surface with a plasma results in the breaking of weak covalent bonds in a polymer due to the bombardment with high-energy particles. The ablation removes outermost molecular layers of the substrate exposed to the plasma. The molecular layers are sputtered off, or are reduced to such low molecular weight that they evaporate off, and can be removed by a vacuum. Because the chemistry of most layers of surface contamination is generally composed of organic compounds, plasma treatment can remove contaminants such as oil films or molding additives.

It is expected that the plasma ablated surface is more uniformly clean and a more active polymer surface. Thus, in some embodiments, the plasma ablated surface has increased adhesion with a coating polymer.

Mechanical Surface Roughening

In several embodiments, mechanical methods may be used to increase the surface roughness of the surface of a polymeric stent to increase the surface area. The increase in surface roughness or surface area tends to increase the adhesion of a coating disposed over the roughened surface. Embodiments of mechanical methods for roughening a polymer stent surface may include abrasive blasting of a polymer stent surface such as bead blasting and sand blasting, or immersion in agitated particle dispersion in a fluid (liquid or gas), but are not limited thereto.

A rough surface refers to a surface having ridges and projections on the surface. A "smooth surface" refers to a surface that is continuous and even. The roughness of a surface or deviation from a smooth surface can be measured by roughness factor (rugosity) of a surface which is given by the ratio:

$$f_r = A_r / A_g$$

where $A_r$ is the real (true, actual) surface (interface) area and $A_g$ is the geometric surface (interface) area free of ridges and projections that cause the roughness. 1986, 58, 439 IUPAC Compendium of Chemical Terminology 2nd Edition (1997). A smooth surface corresponds to a mathematical representation of a surface, such as a cylindrical surface of a tube. "Substantially smooth" refers to a surface that is free or relatively free of ridges, projections, or deviations from, for example, a mathematical surface such as a cylindrical surface. In the case of a tube, the geometric surface area is the surface area of a section of a smooth cylindrical surface and the real surface area is the actual surface area of such a section taking into account deviations from the smooth cylindrical surface due to ridges, projections, etc. Substantially smooth can refer to a surface having a roughness factor typical of a tube fabricated from extrusion.

Blasting Embodiments

Certain embodiments of the present invention include the use of abrasive blasting to increase the roughness of a polymer stent surface. Abrasive blasting refers generally to propelling particulate material at high-velocity at a surface of a substrate in a manner than increases the roughness of the surface. Such methods can include sand blasting or bead blasting. In such embodiments, a stream of particles is directed at a polymer stent surface in a manner that etches the surface, thus increases the surface roughness of at least a portion of the polymer surface. "Etching" refers to producing a regular or irregular pattern on a material by indentation or remove of material from the material's surface. The degree or roughening can be controlled by a several factors including the particles size, particle velocity, density of particles in particles stream, and the mass of the particles.

Abrasive blasting systems are known and commercially available. An abrasive blasting system generally includes: the abrasive or particulate matter, an air compressor, and a blaster gun. The system generates a pressurized abrasive gas stream from the blaster gun with abrasive mixed or dispersed therein. For abrading a small object, such as a stent, the system includes a fixture for holding the object during abrasive treatment. The system additionally can include a collector, such as a vacuum system, to gather up particulate material and material removed from the substrate. The pressurized gas can include gases including, but not limited to, air, nitrogen, argon, carbon dioxide, or a combination thereof. In other embodiments, the gas may include a solvent for the surface polymer.

Various types of particulate matter may be used in embodiments of the present invention. Exemplary classes of materials include metals, metallic salts, ceramics, polymers, and combinations thereof Exemplary materials are provided below. As indicated above, the degree of roughness imparted by the abrasive process can depend on the particles size. It is expected that the scale of indentations and protrusions imparted are similar to the particle size. Thus, the particle size of the abrasive material can be adjusted to obtain a desired degree of roughness and length scale of indentations and protrusions.

Figure 3:
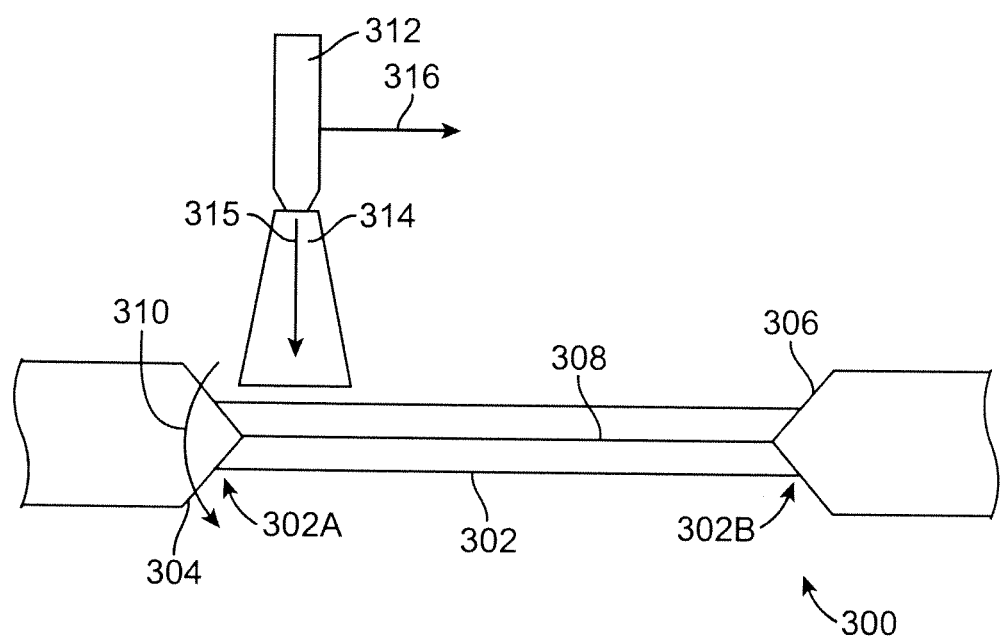
FIG. 3 depicts a stent mounted on a cone mandrel support receiving a surface roughening treatment.

In certain embodiments of abrasive treatment, a stent is mounted on stent support, such as a mandrel, which is supported by a fixture. The mandrel can be configured to allow uniform or near uniform exposure of the stent surface to the stream of abrasive. Additionally, the nozzle and stent can be configured to move relative to one another to maximize the surface area of the stent abraded by the abrasive treatment. FIG. 3 depicts an exemplary system 300 for abrasive treatment of a stent. A stent 302 is supported by mandrel including a cone member 304 and a cone member 306 with a wire 308 extending between the cone members. A proximal end 302A of stent 302 is supported by cone member 304 and a distal end 302B of stent 302 is supported by cone member 306. One or both of the cone support members are affixed to rotatable fixture (not shown) that allows rotation of stent 302 as shown by an arrow 310. A nozzle 312 propels stream of abrasive mixture 314 onto stent 302, as shown by an arrow 315. Additionally, nozzle 312 translates along the axis of stent 302 as shown by an arrow 316.

Additionally, following the abrasive treatment, the stent can be processed to remove abrasive particulate matter adhered to the abraded surface. In one embodiment, the stent can be treated, such as by dipping or spraying, with a fluid that is inert to the polymer surface of the stent. For example, the stent can be treated with an aqueous fluid or an organic fluid that is a nonsolvent for the polymer. A pressurized gas stream free of abrasive material can also be used to remove adhered particulate matter. In addition, adhered matter can also be removed disposing the stent in a liquid such as water (e.g., deionized water) or a nonsolvent and sonicating the liquid.

In some embodiments, the particles can have a characteristic length, such as a diameter, between about 0.2 microns and about 15 microns. It is believed that if the particles are small enough, treatment of a surface may not increase the surface roughness and may even polish the stent surface, i.e., make the surface smoother. The particles can be composed of materials including, but not limited to, silicon, silicon carbide, aluminum oxide, sodium chloride, sodium phosphate, bicarbonate of soda, calcium carbonate, irregular particles of glass, quartz, silicon carbide, tungsten carbide, alumina, zirconia, calcium salts, magnesium salts, tungsten, tungsten alloys, stainless steels, and cobalt chrome alloys. In certain embodiments the abrasive particles are high in density and comprise metals and high density ceramics.

Exposing Stent Surface to Gas Mixed with Abrasive Material in a Chamber

Other embodiments of treating a polymeric surface of a stent with a particle gas mixture can include disposed a stent in a chamber with abrasive material and inducing movement or flow of the particles to abrade the stent surface. In one exemplary embodiment, a stent is placed in a container along with abrasive particles and the container is agitated. In certain embodiments, the agitation occurs by shaking, vibrating, rotating, or generally moving the container in manner that generates movement of the particles across the stent surface in a manner that abrades the stent surface. In an exemplary embodiment, an elongate container, such as a cylindrical container, may be rotated about its cylindrical axis, or end over end. In some embodiments, the container may be only partially filled with abrasive media, for example, ½, ⅔, or ¾ filled by volume.

Fluidized Bed

In further embodiments, a polymer surface of a stent can be abraded by exposing the stent to an agitated particulate gaseous suspension. An agitated particle suspension refers to a particulate matter that is suspended and undergoes constant movement. In some embodiments, a stent can be supported within a chamber including the agitated suspension. In some embodiments, an agitated particle suspension can be formed through introduction of pressurized gas into a vessel or container holding a particulate medium. In such embodiments, the particulate medium present in a vessel can exhibit properties characteristic of a fluid, such as the ability to free-flow under gravity, or to pumped using fluid type technologies. In some embodiments, the agitated particle suspension is a fluidized bed which refers to a bed of solid particles with a stream of air or gas passing upward through the particles at a rate great enough to set them in motion. The degree of abrasion can depend on the velocity of the particles, the flow rate of pressurized gas, the pressure of the gas, and the density of the particles in the vessel. The suspension have less than 5 vol %, 20-30 vol %, 30-50 vol %, or greater than 50 vol % of particles.

Figure 4A:
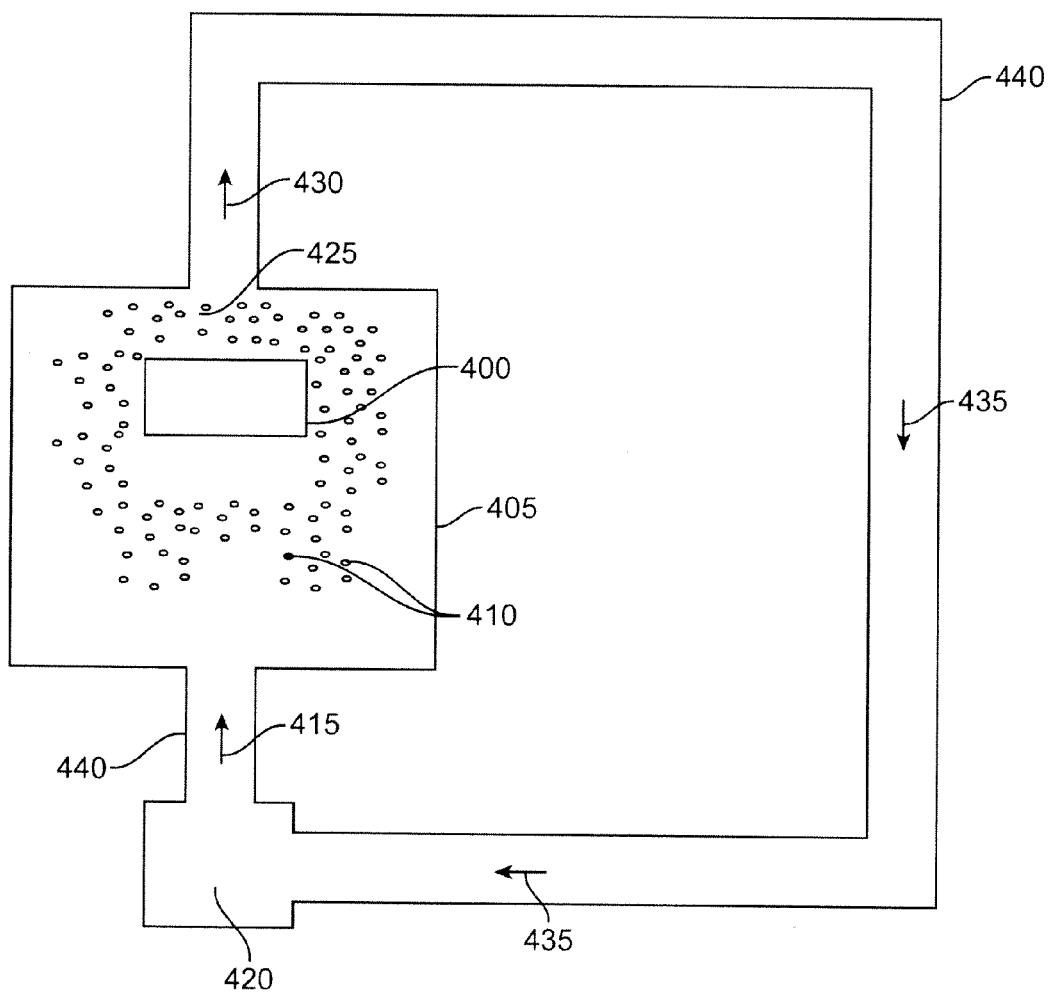
FIG. 4A depicts a stent roughening apparatus utilizing an agitated particle dispersion.

An exemplary embodiment of abrasion of the polymeric surface of a stent is depicted in FIG. 4A. FIG. 4A depicts a stent 400 in a container 405 containing particles 410. The embodiment of FIG. 4A is also similar to a fluidized bed. A gas is blown into container 410, as shown by an arrow 415, by a pump or a blower 420. The gas induces movement of particles 410 which abrade the polymeric surface of stent 400. The gas can be a solvent vapor or a gas mixture including a solvent for the surface polymer and a nonsolvent for the surface polymer. It is believed that the solvent can facilitate etching of the surface, and thus, increasing the surface roughness. Alternatively, the gas can be a nonsolvent for the surface polymer such as air, nitrogen, oxygen, argon, etc.

Gas exits container 410 at air outlet 425, as shown by an arrow 430. Gas can be recirculated to pump or blower 420 through tube 440, as shown by arrows 435. Air outlet 425 can have a filter to prevent particles from entering tube 440. Alternatively, the gas may not be recirculated.

Exposing Stent Surface to Liquid Abrasive Medium

Additional embodiments of abrading a polymeric surface of a stent include contacting a polymeric surface of a stent with a liquid medium. In some embodiments, the liquid medium can be mixed with abrasive particles, forming an abrasive liquid suspension. In certain embodiments, the liquid medium can include a solvent for the surface polymer that is capable of dissolving the surface polymer. In other embodiments, the liquid medium can be a nonsolvent for the surface polymer that is not capable of dissolving the surface polymer. An abrasive liquid suspension with a solvent, the surface can be modified by dissolving at least a portion of the surface polymer. The particles can modify the polymeric surface by abrading the polymeric surface. Several embodiments of abrading a polymer surface of a stent with a liquid medium are analogous to the embodiments described above using gas/particles mixtures.

Water Jet

In certain embodiments, a polymer surface of a stent can be abraded or roughened by a high-velocity, pressurized stream of liquid. In some embodiments, the stream of fluid can be a concentrated jet of liquid, free or substantially free of gas bubbles. The stream can be directed onto a polymer surface of a stent in a manner that increases the surface roughness of the stent. The degree of abrasion depends on factors such as the velocity of the stream and the radial cross-section of the stream. The liquid can be water or an organic liquid. The organic liquid can be solvent or a nonsolvent for the surface polymer. In further embodiments, the liquid stream can include an abrasive particulate material. Water jet cutting is known and used for cutting and abrasion of surface and can be adapted to abrasion of polymer stent surfaces with water and other liquids.

A system for liquid abrasion of a polymer stent surface can include a nozzle connected to a high-pressure pump. The liquid is then ejected out of the nozzle onto a polymer stent material by bombarding it with the stream of high-speed water. Abrasive materials can be mixed with the water at or before the nozzle. An exemplary system for liquid abrasion of a polymer stent is similar to that depicted in FIG. 3. Nozzle 312 can eject a stream of fluid onto the surface of stent 302. In some embodiments, the nozzle can eject a pulsating jet of fluid onto the stent surface.

In additional embodiments, a polymer surface of a stent can be abraded or roughened by an atomized stream of liquid directed onto a surface of a stent. An atomized stream of liquid is composed of fine droplets of liquid mixed with a gas. In some embodiments, the atomized stream of liquid can further include an abrasive material. Spray devices that produce a stream of atomized droplets are known and used for spray coating of devices such as stents. A spray apparatus, such as EFD 780S spray device with VALVEMATE 7040 control system (manufactured by EFD Inc., East Providence, R.I.) is a spray device with an air-assisted external mixing atomizer. Such a spray device produces an atomized stream from a mixture of liquid and gas.

In additional embodiments, a polymer surface of a stent can be abraded by exposing the stent to an agitated particulate liquid suspension. In such embodiments, stent can be disposed in a vessel containing a liquid particles suspension. The stent can be supported on a fixture or allowed free to translate through the suspension. The liquid particulate suspension can be agitated in a number of ways. In one embodiment, the vessel can be agitated by shaking, vibrating, rotating, or generally moving the container in manner that generates movement of the particles across the stent surface to abrade the stent surface. In other embodiments, the liquid particle suspension can be agitated through introduction of pressurized gas into the vessel or container holding suspension. In another embodiment, the suspension can be stirred by a mechanical mixer or ultrasonic mixing.

Brush

In some embodiments, a polymer stent surface can be roughened through application of an abrasive member to a stent surface. In some embodiments, the abrasive member can be a brush. In such embodiments, a brush having metallic wire bristles or more generally bristles stiff enough to roughen the polymeric stent surface. Examples of brushes include, but are not limited to, brushes composed of arrays of metallic wires, ceramic wires, glass wires, wires with abrasive media affixed to them, and wires of very hard polymers or reinforced polymers. In other embodiments, an abrasive member can have a surface of sand paper or emery cloth.

In certain embodiments, a cylindrical brush can be drawn through the lumen of the stent so that the outside surface of the brush roughens the luminal surfaces and a portion of the sidewalls. A stent drawn through the inside of a hollow cylindrical brush so that the inside surface of the brush roughens the abluminal surface of the stent. The stent can be placed on a mandrel and then pushed though the annulus.

Figure 4B:
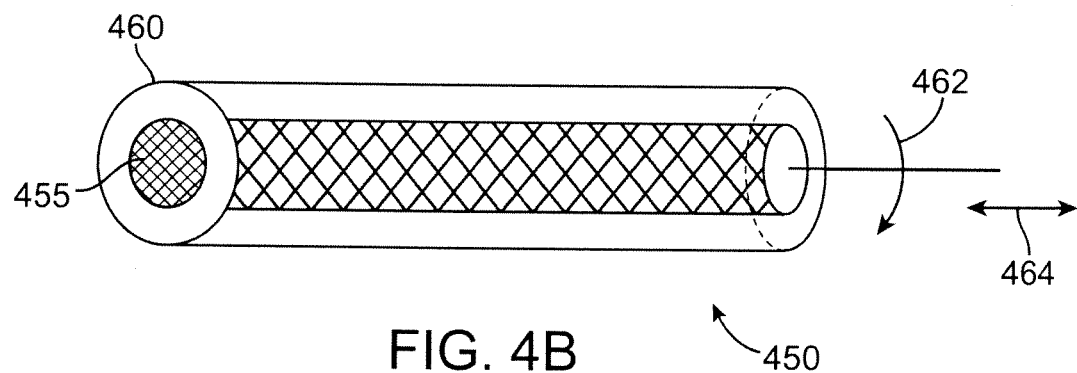
FIG. 4B depicts a stent luminal surface roughening apparatus utilizing a brush.
Figure 4C:
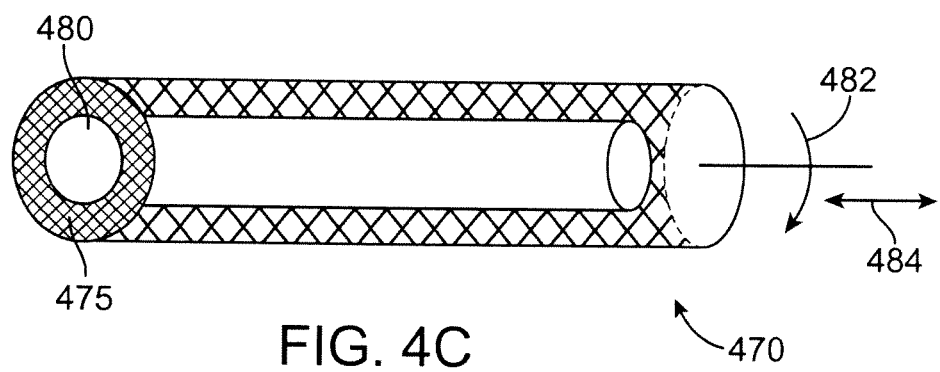
FIG. 4C depicts a stent abluminal surface roughening apparatus utilizing a brush.

In certain embodiments, a stent can be disposed on a rotatable support with a fixed cylindrical brush disposed within or around the outside of the stent. The luminal or abluminal surface and at least a portion of the sidewalls of the stent are roughened through rotation of the stent relative to the brush. Alternatively, the brush can be rotated relative to the stent. In further embodiments, the stent or brush can be translated relative to one another. In an embodiment 450 as illustrated in FIG. 4B, the luminal surface of stent 460 is roughened by brush 455 by rotating brush 455 in direction 462, and/or translating brush 455 in direction 464. In an additional embodiment 470 as illustrated by FIG. 4C, the roughening of the abluminal surface of stent 480 by using brush 475 occurs when brush 475 is rotated in direction 482 and/or simultaneously translated in direction 484.

Surface Swelling/Etching

In further embodiments, the adhesion of coating to a polymer surface of a stent can be improved through treatment of the polymer surface with a solvent or a mixture of solvents. Some embodiments of the treatment can include applying a solvent onto the polymer surface, followed by removal of at least some of the solvent. A coating may then be applied to the treated surface that includes some of the solvent or a treated surface that free or substantially free of solvent. The roughness of the polymer surface increased by the treatment which enhances the adhesion of a coating layer applied to the treated surface. The polymer stent surface may be roughened by a swelling, dissolution or etching of a surface polymer, or a combination of both.

As is understood by persons of skill in the art, swelling of a polymer occurs when a solvent in contact with a sample of the polymer diffuses into the polymer. L. H. Sperling, Physical Polymer Science, $3^{rd}$ ed., Wiley (2001). Thus, a swollen polymer sample includes solvent molecules dispersed within the bulk of the polymer. Dissolution of the polymer occurs when polymer molecules diffuse out of the swollen polymer into solution.

"Solvent" for a given polymer can be defined as a substance capable of dissolving or dispersing the polymer or capable of at least partially dissolving or dispersing the polymer to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. A substance incapable or substantially incapable of dissolving a polymer should be capable of dissolving only less than 0.1 mg of the polymer in 1 ml of the non-solvent at ambient temperature and ambient pressure, and more narrowly only less than 0.05 mg in 1 ml at ambient temperature and ambient pressure. A substance incapable or substantially incapable of dissolving a given polymer is generally referred to as a nonsolvent for that polymer. A nonsolvent or a poor solvent may be capable of swelling a polymer.

Solvents and nonsolvents for polymers can be found in standard texts (e.g., see Fuchs, in Polymer Handbook, 3rd Edition and Deasy, Microencapsulation and Related Drug Processes, 1984, Marcel Dekker, Inc., N.Y.). The ability of a polymer to swell and to dissolve in a solvent can be estimated using the Cohesive Energy Density Concept (CED) and related solubility parameter values as discussed by Deasy and can be found in detail in the article by Grulke in Polymer Handbook. Thus, a person skilled in the art will be able to select a solvent that is capable of swelling the surface polymer and is incapable or substantially incapable of dissolving the surface polymer.

Treating with Poor Solvent

In certain embodiments, a polymer stent surface is treated with a solvent. In some embodiments, the solvent is a nonsolvent or a poor solvent that swells and dissolves little or none of the surface polymer. In other embodiments, the treatment solvent dissolves or etches the surface polymer and swells the surface polymer.

In some embodiments, the solvent is applied to the surface in an amount such that there is a layer or film of solvent present on the surface. In such an embodiment, a layer of solvent may be present over all or majority of the surface area of the stent to be treated. In these embodiments, a solvent can be selected that exhibits a high degree of wetting of the surface. "Wetting" refers to the degree to which a liquid maintains contact with a surface. Poor wetting is indicated by liquids beading up on a surface and good wetting is indicated by a continuous sheet of liquid forming on the surface.

Figure 5:
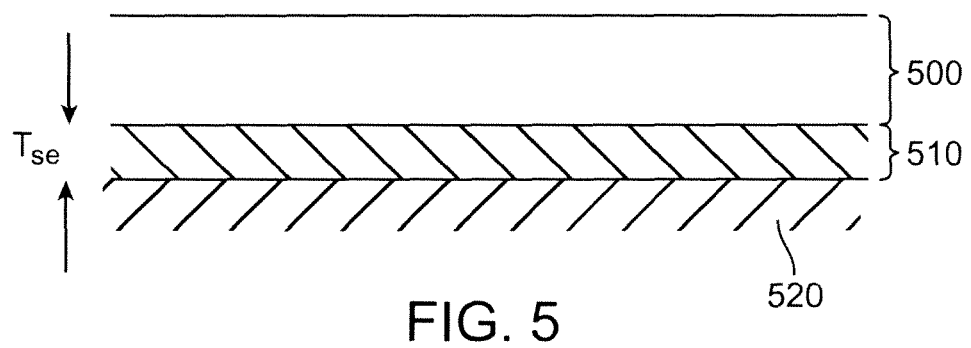
FIG. 5 depicts a cross-section of a solvent roughened stent surface with a coating layer over a substrate.

In some embodiments, the solvent may swell at least a portion of the surface polymer. In an embodiment, the applied solvent may form a swollen of surface polymer over unswollen surface polymer. FIG. 5 depicts a cross-section of a stent showing a solvent layer 500 over a swollen surface polymer layer 510. Swollen surface polymer layer 510 is over an unswollen surface polymer layer 520. In the case of a treatment solvent that dissolves surface polymer, layer 510 includes dissolved surface polymer. As indicated above, unswollen surface polymer 520 can be a substrate of the stent. As shown, swollen surface polymer layer 510 has a thickness Tse.

In such embodiments, the solvent is applied to the surface of the polymer by methods such as spraying or dipping. In an exemplary treating embodiment, the stent mounted on a rotatable support is rotated and translated under a spray nozzle that sprays the solvent onto the stent surface. The stent may be passed 1-5 times or more than 5 times under the spray nozzle. In other embodiments, the stent can be disposed in a solvent bath for a period of time, for example 1-5 seconds, 5-30 seconds, or more than 30 seconds. The solvent layer can be allowed to remain on the surface for a period of time, for example, 1-5 seconds, 5-30 seconds, or more than 30 seconds.

Following application and wetting of the surface polymer with the solvent, the treatment method includes removal of some or all of the solvent from the stent surface. In some embodiments, the all or substantially all of the solvent layer is removed while leaving the swollen polymer layer. In other embodiments, the solvent layer and all or substantially all of the solvent in the swollen polymer is removed.

In general, it is believed that a rapid removal of the solvent may facilitate roughening of the surface polymer and thus adhesion improvement. In some embodiments, the solvent can be removed by blowing gas stream over the stent surface. The gas stream can be air, nitrogen, oxygen, argon, or other gas. The gas stream can be room temperature air, i.e., 20-30° C. Alternatively, the gas stream can be heated to a temperature between 30-50° C. or greater than 50° C.

In other embodiments, the solvent can be removed by allowing the solvent to evaporate without assistance of a gas stream at or near room temperature for a period of time. The drying period may be less than 10 minutes, 10-20 minutes, 20-30 minutes, or greater than 30 minutes. In some embodiments, a high volatile solvent is used with a relatively high evaporation rate. Such a solvent may be one that can evaporate completely from the surface of the stent in less than 5-20 minutes. In other embodiments, the solvent can be removed by allowing the solvent to evaporate without assistance of a gas stream above room temperature, for example, between 30-50° C. or greater than 50° C. In some embodiments, the treated surface has increased roughness has increased adhesion with a coating polymer.

After removal of some or all of the solvent, the polymer surface of the stent can be coated with a polymer that can include a drug. A coating material including a coating polymer dissolved in a coating solvent and a drug mixed with the coating solvent. The coating material can be applied by methods such as spraying or dipping followed by removal of coating solvent to form the coating over the surface polymer.

In some embodiments, the coating material can be applied over the polymer surface having at least some of the solvent layer. In other embodiments, the coating material can be applied to the polymer surface that is free or substantially free of the solvent layer over the swelled region. Additionally, the coating material is applied to a surface polymer free or substantially free of the solvent layer.

In an exemplary embodiment, the surface polymer is PDLA of a stent formed from PLLA. Exemplary treatment solvents include acetone, methylene chloride, tetrahydrofuran (THF), cyclohexane, chloroform, dimethyl chloroform, and combinations thereof. An exemplary weak or poor solvent treatment solvent is acetone which tends to swell, but not dissolve PLLA. Exemplary good solvent that swells and dissolves or etches PLLA include chloroform and dimethyl chloroform. Cyclohexane is a weaker solvent than THF. A solvent intermediate between weak and strong solvents is THF. An exemplary coating polymer can be PDLA dissolved in acetone coating solvent.

Treatment with a Mixture of Solvents

In further embodiments, the treatment solvent can be solvent system that includes a mixture of two or more solvents. In some of these embodiments, the solvent system can include solvents that are of different strengths with respect to the surface polymer. The solvent system can include a weak solvent and a strong solvent. The weak solvent may swell, but not dissolve the surface polymer while the strong solvent dissolves and swells the surface polymer. An exemplary solvent system includes acetone and chloroform. Additional solvents include IPA and chloroform, but are not limited thereto.

In other embodiments, the solvent system can include a solvent having a higher evaporation rate or of a greater volatility than another solvent in the solvent system. Evaporation rate refers to the mass of material that evaporates from a surface per unit time (e.g., 3 grams per square meter per hour). A dimensionless evaporation rate can be defined as the rate at which a material will vaporize (evaporate, change from liquid to vapor) compared to the rate of vaporization of a specific known material. The general reference material for evaporation rates is n-butyl acetate. The ratios for some exemplarily solvents are as follows: acetone (5.6), chloroform (11.6), tetrahydrofuran (8.0), cyclohexane (2.6), ethanol (2.7), methylene chloride (27.5), dimethylacetamide (<0.17), dimethyl sulfoxide (4.3). In some embodiments, the solvent system includes two solvents with a ratio of evaporation rates of 1-1.5, 1.5-2, 2-5, or greater than 5. Exemplary solvent systems with ratio of evaporation rates include chloroform/acetone (2.1), tetrahydrofuran/acetone (1.4), acetone/cyclohexane (2.2), methylene chloride/acetone (4.9), methylene chloride/ethanol (10.2), but are not limited thereto.

In additional embodiments, the solvents of the solvent system are miscible. Alternatively, two or more of the solvents are immiscible.

Treatment with a solvent system with solvent having different strengths, evaporation rates, or both facilitates increasing the roughness of the polymer surface of the stent.

Phase Inversion

In some embodiments, a phase inversion method is used to roughen a polymer surface of a stent to improve adhesion of a coating. In such embodiments, a solvent capable of dissolving the surface polymer is applied to a stent from a solvent layer on the surface, as described above. Additionally, the applied solvent is miscible with phase inversion fluid. In some embodiments, the phase inversion fluid is water. Next, the stent is exposed to the phase inversion fluid, thereby causing the dissolved surface polymer in the solvent surface layer to precipitate out. The exposure to water can include exposure to a gaseous environment with a high percentage of the phase inversion fluid. For example, the stent can be exposure to high humidity environment, for example, at least 70%, 80%, 90%, or 100% humidity. In other embodiments, the stent can be dipped in or sprayed with the phase inversion fluid in liquid form The phase inversion fluid may also be a non-polar nonsolvent.

In an exemplary embodiment, the surface polymer is PLLA. Exemplary solvents useful in the phase inversion method include, but are not limited to, dimethylacetamide (DMAC), dimethyl sulfoxide (DMSO), hexafluoroisopropanol and 2,2,2-trifluoroethanol. In an embodiment, a PLA stent is sprayed with DMSO and then air with 100% humidity is directed to the treated surface. The resulting treated surface should increase the adherence of a later added coating layer. In another embodiment, a PLLA stent is dipped briefly in DMAC and then dipped into water, resulting in a roughened surface that should increase the adherence of a coating layer. Any combination of dipping or spraying procedures may be used to treat the polymer surface.

Coating Method

In an exemplary embodiment of a coating procedure, a treated stent having a substrate of PLLA is coated with PDLA. The coating material is PDLA dissolved in acetone. The weight fraction of solvent in coating material can be greater than 50%, 70%, 80%, 95%, or more narrowly, 97%. The spray nozzle forms an atomized stream of coating material for application on the stent. The spray nozzle temperature or atomization temperature can be between about 15° C. and 30° C. Atomization pressure can be between 5.5 psi and 7 psi. A temperature of heated air from a heat nozzle directed at the stent can be between 38° C. and 40° C. The air pressure of the nozzle can be between 18 psi and 22 psi. The syringe pump rate can be between 2 ml/hr and 6 ml/hr.

Adhesion Promoting Layer

Embodiments of the present invention include an implantable medical device including an adhesion promoting layer between a therapeutic layer and polymer surface of the device. In some embodiment, the promoting layer includes a block copolymer with an outer block and an anchor block. In some embodiments, the outer block, the anchor block, or both can be bioabsorbable polymers. In addition, the anchor block is miscible with the surface polymer and the outer block is miscible with the therapeutic layer. Additionally, the therapeutic layer may contain an active agent or drug mixed or dispersed within a polymer.

In other embodiments, the adhesion promoting layer includes a copolymer having some units that are miscible in the surface polymer and some that are miscible in the therapeutic layer.

In such embodiments, the block copolymer adhesion promoting layer can have more than one outer block and more than one anchor block. In one embodiment, the block copolymer can have an outer block on one end and an anchor block at another end. In another embodiment, the block copolymer can have an outer block between two anchor blocks or anchor block between two outer blocks.

Figure 6A:
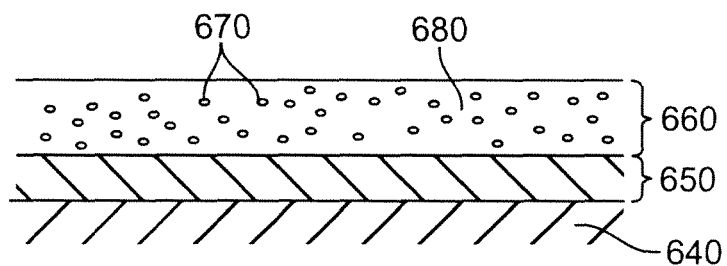
FIG. 6A depicts a cross-section of a stent showing a coating material layer over a swollen surface polymer layer.

FIG. 6A depicts a cross-section of a substrate 640 of a stent with an adhesion promoting layer 650 disposed over substrate 640. A therapeutic layer 660 is disposed over adhesion promoting layer 650. Therapeutic layer 660 includes a drug 670 dispersed within a polymer 680. Adhesion promoting layer 650 improves the adhesion of drug-polymer layer 660 to substrate 640.

As indicated above, the anchor block of the block copolymer of the adhesion promoting layer is miscible with the surface polymer. In one embodiment, the anchor block can have the same chemical composition as the surface polymer. Alternatively, the anchor block can have a chemical composition different from the surface polymer, but similar enough so that the anchor block is miscible with the surface polymer. In an exemplary embodiment, the block copolymer of the adhesion promoting layer can have a PLLA anchor block and be disposed over a PLLA surface, which can be the surface of a PLLA stent substrate.

In some embodiments, the adhesion promoting layer can be applied to a polymer surface so that at least some of the outer blocks of the block copolymers are mixed within the therapeutic layer. Additionally, anchor blocks can be mixed within the surface polymer. The anchor blocks of the block copolymer act as a compatibilizer that strengthens the bond between the adhesion promoting layer and the surface polymer. Similarly, the outer blocks of the block copolymer act as a compatibilizer that strengthens the bond between the adhesion promoting layer and the therapeutic layer.

Figure 6B:
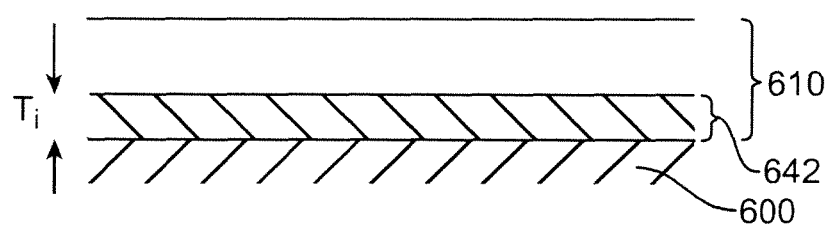
FIG. 6B depicts a cross-section of a stent polymer surface with a copolymer adhesion promoting layer over a substrate of the stent showing an interfacial region.

FIG. 6B depicts a cross-section of a stent surface with an adhesion promoting layer 610 over a substrate 600. Adhesion promoting layer 610 can be applied to form an interfacial region 642 which can include anchor blocks mixed with substrate polymer. A thickness Ti of interfacial region 642 can be varied depending on coating application processing parameters The enhanced adhesion can allow the use of a tough, high fracture resistant coating that may otherwise have poor adhesion to a polymer substrate of a device. The polymer material for a substrate of a device, such as a stent, may be selected primarily on the basis of strength and stiffness so that the stent substrate can provide support for a lumen. Such substrate polymers tend to be crystalline or semi-crystalline polymers that are glassy or have a Tg above body temperature. Such glassy substrate polymers include PLLA.

In exemplary embodiments, the molecular weight of the outer blocks can be between 20 kg/mol and 150 kg/mol, or greater than 150 kg/mol. In exemplary embodiments, the molecular weight of the anchor blocks can be between 20 kg/mol and 150 kg/mol, or greater than 150 kg/mol. The relative weight percent of the outer blocks and the anchor blocks can be between 1:5 and 5:1.

Embodiments of the block copolymers disclosed herein can be formed by solution-based polymerization. Other methods of forming the block copolymers are also possible, such as, without limitation, melt phase polymerization.

The block copolymer adhesion promoting layer may be formed over an implantable medical device, such as a stent, by applying coating material to a polymer surface of the device. The coating material can be a solution including the block copolymer. The adhesion promoting layer may be applied to the stent by immersing the device in the coating material, by spraying the composition onto the device, or by other methods known in the art. The solvent in the solution is removed, leaving on the device surfaces the adhesion promoting layer.

In some embodiments, the solvent of the adhesion promoting layer is also a solvent for the surface polymer on which the adhesion promoting layer is applied.

Due to dissolution or swelling of a portion of the surface polymer during application of coating material, the adhesion promoting layer near the surface of the surface polymer includes dissolved surface polymer in addition to the block copolymer from the adhesion promoting layer. It is believed that upon removal of the solvent, an interfacial region, as depicted in FIG. 6B, is formed that includes anchor blocks of the block copolymer adhesion promoting layer mixed with surface polymer. This interfacial region can be formed due to the miscibility of the surface polymer with the anchor blocks.

Figure 6C:
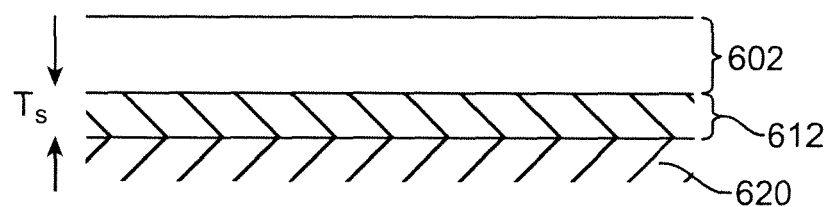
FIG. 6C depicts the cross-section of a stent surface with a drug-polymer layer over a copolymer adhesion promoting layer disposed over a substrate of the stent.

FIG. 6C depicts a cross-section of a stent showing an adhesion promoting layer 602 over a swollen surface polymer layer 612. Swollen surface polymer layer 612 is over unswollen surface polymer substrate 620. As shown, swollen surface polymer layer 612 has a thickness Ts. Due to swelling of the surface polymer in swollen polymer layer 612, it is believed that anchor blocks of the block copolymer in adhesion promoting layer 602 penetrate into or mix with the surface polymer in swollen polymer layer 612 prior to removal of the solvent. Upon removal of the solvent, a coating layer is formed over substrate 620. In some embodiments, a polymeric surface layer can be pretreated with a solvent that dissolves or swells the surface polymer prior to applying an adhesion promoting layer. Following pretreatment, the adhesion promoting layer can be applied over the pretreated surface.

Figure 6D:
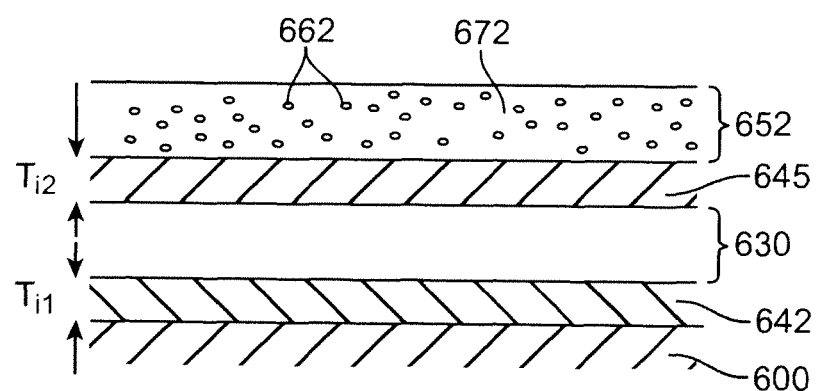
FIG. 6D depicts the cross-section of a stent with an adhesion promoting layer disposed over the substrate and a therapeutic layer disposed over the adhesion promoting layer.

In other embodiments, a therapeutic layer is applied over the adhesion promoting layer that has been applied to a polymeric surface. A therapeutic polymer layer can then be formed over the block copolymer adhesion promoting layer. A coating material includes a therapeutic coating polymer dissolved in a solvent and a drug. FIG. 6D depicts a drug layer 652 over an adhesion promoting layer 630. Drug layer 652 includes a drug 662 mixed or dispersed within a polymer 672. A first interfacial layer 642 of thickness $Ti_1$, discussed above, includes anchor blocks and the surface polymer 600. A second interfacial layer 645 of thickness $Ti_2$ is located between drug layer 652 and adhesion promoting layer 630. This interfacial layer may include polymer from the drug layer 652 and outer blocks from adhesion promoting layer 630. Thus, improved adhesion of drug layer 652 is accomplished by strengthening the bond between drug layer 652 and adhesion promoting layer 630, as well as strengthening the bond between adhesion promoting layer 630 and surface polymer 600.

In exemplary embodiments, a stent substrate of scaffolding is PLLA and the therapeutic layer is PDLA. In such embodiments, the adhesion coating layer can include, but is not limited to PLLA-b-PDLA, PLLA-co-PDLA and PLLA-co-PLGA. Additionally, polyethylene (PEG) is compatible with PLLA and PPG (polypropylene glycol) is compatible with PDLA. Thus, the adhesion promoting layer can include PDLA-b-PEG and PPG-b-PEG.

In exemplary embodiments, the adhesion promoting layer is about 0.05 μm to about 5 μm. In other embodiments, the thickness is from about 0.1 μm to 1 μm, 0.1 μm to 3 μm, or 0.1 μm to 5 μm.

In general, representative examples of polymers that may be used to fabricated a substrate of and coatings for an implantable device include, but are not limited to, poly(N-acetylglucosamine) (Chitin), Chitosan, poly(hydroxyvalerate), poly(D,L-lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alpha-olefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in embodiments of the present invention include ethylene vinyl alcohol copolymer (commonly known by the generic name EVOH or by the trade name EVAL), poly(butyl methacrylate), poly(vinylidene fluoride-co-hexafluoropropylene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

For the purposes of the present invention, the following terms and definitions apply:

For the purposes of the present invention, the following terms and definitions apply:

Drugs or therapeutic active agent(s) can include anti-inflammatories, antiproliferatives, and other bioactive agents.

An antiproliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), Biolimus A9 (Biosensors International, Singapore), deforolimus, AP23572 (Ariad Pharmaceuticals), prodrugs thereof, co-drugs thereof, and combinations thereof In one embodiment, the anti-proliferative agent is everolimus.

An anti-inflammatory drug can be a steroidal anti-inflammatory agent, a nonsteroidal anti-inflammatory agent, or a combination thereof In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetsol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof In one embodiment, the anti-inflammatory agent is dexamethasone.

Alternatively, the anti-inflammatory may be a biological inhibitor of proinflammatory signaling molecules. Anti-inflammatory biological agents include antibodies to such biological inflammatory signaling molecules.

In addition, drugs or active can be other than antiproliferative agents or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax a (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics; antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable.

EXAMPLES

The examples set forth below are for illustrative purposes only and are in no way meant to limit the invention. The following examples are given to aid in understanding the invention, but it is to be understood that the invention is not limited to the particular materials or procedures of examples.

Example 1

Plasma Treatments

Poly(L-lactide) stents, 12 mm long from Bioabsorbable Vascular Solutions (BVS) are placed onto stainless steel wire mandrels. These mandrels are placed into a Teflon fixture which holds the wires horizontally. This fixture with multiple stents is placed into a March Plasma C-Series Plasma Treater (St. Petersburg, Fla.). Using oxygen as the working gas, the stents are exposed to plasma conditions of 200 watts, approximately 1 liter/minute oxygen flow rate at a pressure of 100 milli-torr for 150 seconds. After removal from the plasma chamber, the stents may be coated with a drug reservoir layer within 12 hours.

Examples 2, 3

Mechanical Roughening

Example 2

A 12 mm long poly(L-lactide) in-house stent is mounted on a mandrel composed of a central stainless steel wire on which are slid two cones via holes in the cones. The cones point inwards and are of such a diameter to hold the stent at its distal and proximal ends. This mandrel is mounted in an apparatus to rotate the stent. A sand blasting apparatus, using compressed nitrogen gas is used to direct sodium chloride particles at the stent while the stent rotates. The sandblasting nozzle translates along the length of the stent. After surface roughening, the stent is gently sonicated in deionized water to remove any adhered or embedded sodium chloride, followed by drying in a vacuum oven or a desiccator.

Example 3

In another example, a 12 mm polylactide in-house is placed in a 20 ml glass vial. The vial is half filled with tungsten powder with an average size of 2 microns (Specialty Chemical Group LLC, Akron Ohio). The vial is rotated end over end at a speed of 30 rpm for 10 minutes.

Example 4

Roughening Using Solvents

A 12 mm poly(L-lactide) in-house stent is mounted in a spray system which both translates and rotates the stent. Methylene chloride is sprayed at the stent in a series of passes at high enough of a flux for liquid methylene chloride to be present on the stent surface, followed by in process drying with room temperature air for 10 seconds. After three passes, the stent is allowed to air dry for 30 minutes before application of the drug reservoir layer.

Example 5

Adhesion Promoting Layer

A PLLA-b-PDLA polymer is synthesized via ring opening polymerization using 1-dodecanol as the initiator with a stannous octoate catalyst. This may be carried out in a toluene solvent, in an argon atmosphere at a temperature of 110° C. D,L-lactide monomer may be added first. After the first monomer is consumed, the L-lactide is added and allowed to polymerize. The polymer is isolated by precipitation into methanol followed by drying in vacuo. The appropriate choice of catalyst/monomer stoichiometry will result in a poly(D,L-lactide-b-L-lactide) with Mw of 80K and 50/50 monomer ratio by weight. This adhesion promoting polymer is applied to a 12 mm poly(L-lactide) in-house stent as a 2% (w/w) solution in chloroform. The stent is rotated at a speed of roughly 200 rpm while passing longitudinally under the spray nozzle, followed by a drying procedure under an air stream at 40° C. for 10 seconds. The coating is applied as a series of spray passes with approximately 10 μg of coating applied per pass. Any remaining solvent is removed by oven drying at 50° C. for one hour resulting in 100 μg of a poly(D,L-lactide-b-L-lactide) adhesion promoting polymer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of improving the adhesion of a polymer coating layer to a stent surface comprising:
   Providing a stent formed from a substrate polymer;
   Treating a polymer surface of the stent with a fluid, wherein the treating increases the roughness of the polymer surface; and
   Forming a coating comprising a coating polymer on the treated stent surface, the increased surface roughness enhancing the adhesion of the coating polymer to the stent surface,
   wherein the fluid comprises a solvent capable of dissolving the substrate polymer and absorbing moisture at the surface of the stent, wherein the treating comprises applying the fluid to the surface of the polymer which at least partially dissolves the polymer and exposing the treated stent to a phase inversion fluid to induce phase inversion, wherein the phase inversion fluid is water or an organic non-polar non-solvent that does not substantially dissolve the surface polymer, wherein the phase inversion fluid causes the dissolved surface polymer in the fluid to precipitate out of solution and causes the roughness of the stent surface to increase due to precipitation of the dissolved polymer induced by phase inversion.

2. The method of claim 1, wherein the fluid comprises a solvent selected from the group consisting of acetone, methyl chloride, methylene chloride, chloroform, tetrahydrofuran, and dimethyl chloroform.

3. The method of claim 1, wherein the treating comprises forming a layer of the fluid over the surface of the stent and removing the layer of fluid by application of heat to the fluid layer.

4. The method of claim 1, wherein the substrate polymer is PLLA and the fluid is a mixture comprising acetone and chloroform.

5. The method of claim 1, wherein the substrate polymer is PLLA and the solvent is selected from the group consisting of DMAC, DMSO, and hexafluoroisopropanol, 2,2,2-trifluoroethanol.

* * * * *